United States Patent
Offermans et al.

(10) Patent No.: US 9,035,362 B2
(45) Date of Patent: May 19, 2015

(54) SENSOR FOR SENSING THE PRESENCE OF AT LEAST ONE FLUIDUM

(71) Applicant: Stichting IMEC Nederland, Eindhoven (NL)

(72) Inventors: Peter Offermans, Eindhoven (NL); Roman Vitushinsky, Vaals (NL); Mercedes Crego Calama, Geldrop-Mierlo (NL); Sywert Brongersma, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 0 days.

(21) Appl. No.: 13/909,937

(22) Filed: Jun. 4, 2013

(65) Prior Publication Data

US 2013/0334061 A1    Dec. 19, 2013

(30) Foreign Application Priority Data

Jun. 7, 2012    (EP) ..................................... 12171170

(51) Int. Cl.
| | | |
|---|---|---|
| *G01N 27/403* | (2006.01) | |
| *H01L 29/15* | (2006.01) | |
| *H01L 29/66* | (2006.01) | |
| *H01L 21/00* | (2006.01) | |
| *G01N 27/414* | (2006.01) | |

(52) U.S. Cl.
CPC ........ *G01N 27/4146* (2013.01); *G01N 27/4143* (2013.01)

(58) Field of Classification Search
CPC ............ G01N 27/4146; G01N 27/414; G01N 27/4143

USPC ...................... 257/253, 328, 192, 76; 438/49; 205/775; 435/7.1; 600/348

See application file for complete search history.

(56) References Cited

U.S. PATENT DOCUMENTS

| | | | | |
|---|---|---|---|---|
| 4,020,830 | A * | 5/1977 | Johnson et al. ................ | 600/348 |
| 6,361,958 | B1 * | 3/2002 | Shieh et al. ..................... | 435/7.1 |
| 7,759,710 | B1 * | 7/2010 | Chiu et al. ...................... | 257/253 |
| 2005/0097941 | A1 * | 5/2005 | Sandvik et al. .............. | 73/31.06 |
| 2005/0110053 | A1 | 5/2005 | Shur et al. | |

(Continued)

OTHER PUBLICATIONS

J. Schalwig et al "Gas sensitive GaN/AlGaN heterostructures", Sensors and Actuators B 87, p. 425-430 (2002).*

(Continued)

*Primary Examiner* — Long K Tran
*Assistant Examiner* — Dzung Tran
(74) *Attorney, Agent, or Firm* — Knobbe, Martens, Olson & Bear LLP

(57) ABSTRACT

A Sensor for sensing the presence of at least one fluidum in a space adjoining the sensor is disclosed. In one aspect, the sensor has a two-dimensional electron gas (2DEG) layer stack, a gate electrode overlaying at least part of the 2DEG layer stack for electrostatically controlling electron density of a 2DEG in the 2DEG layer stack and a source and a drain electrode contacting the 2DEG layer stack for electrically contacting the 2DEG, wherein a detection opening is provided in between the gate electrode and the 2DEG layer stack and wherein the detection opening communicates with the space through a detection opening inlet such that molecules of the fluidum can move from the adjoining space through the detection opening inlet into the detection opening where they can measurably alter a electric characteristic of the 2DEG.

18 Claims, 1 Drawing Sheet

(56) References Cited

U.S. PATENT DOCUMENTS

| | | | |
|---|---|---|---|
| 2005/0263790 A1* | 12/2005 | Moon et al. | 257/194 |
| 2005/0285155 A1* | 12/2005 | Johnson et al. | 257/253 |
| 2008/0203431 A1 | 8/2008 | Garcia et al. | |
| 2008/0302672 A1 | 12/2008 | Sandvik et al. | |
| 2009/0085071 A1 | 4/2009 | Brongersma et al. | |

OTHER PUBLICATIONS

Extended European Search Report issued Nov. 14, 2012 for EP Application No. 12171170.9.

Prokopuk et al., "Development of GaN-based Micro Chemical Sensor Nodes," IEEE Sensors, pp. 199-202, 2005.

* cited by examiner

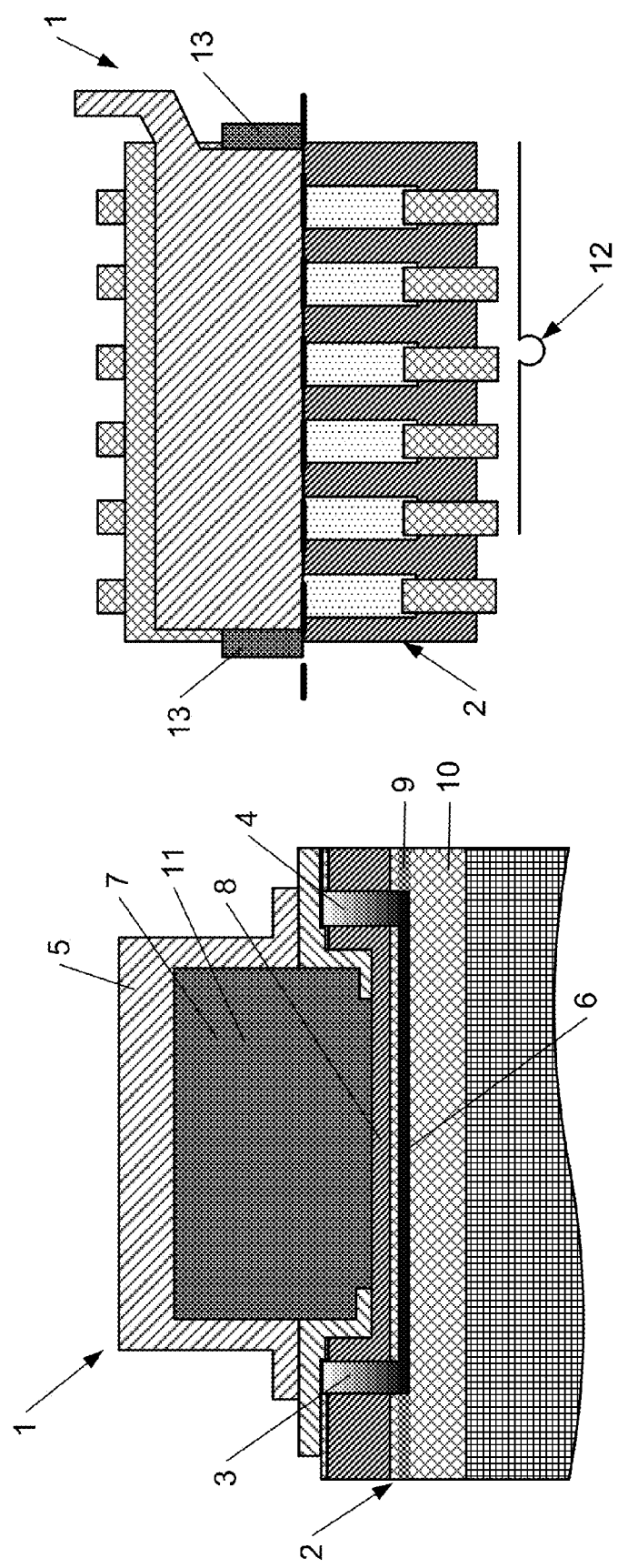

SENSOR FOR SENSING THE PRESENCE OF AT LEAST ONE FLUIDUM

BACKGROUND OF THE INVENTION

1. Field of the Invention

The disclosed technology relates to a sensor for sensing the presence of at least one fluidum in an adjoining space, to the use of a sensor for sensing at least one fluidum in an adjoining space and a method for making such sensor.

2. Description of the Related Technology

Sensors of that kind are already known to the person skilled in the art. The article "Development of GaN-based Micro Chemical Sensor Nodes" by Nicholas Prokopuk, Kyung-Ah Son, Thomas George and Jeong S. Moon published in IEEE sensors 2005, for example, describes a sensor for sensing the presence of at least one fluidum, in this case a gas, in an adjoining space. The sensor comprises HEMT with a two-dimensional electron gas (2DEG) layer stack comprising an AlGaN layer and a GaN layer. A gate overlays at least part of the 2DEG layer stack and electrostatically controls electron density of a 2DEG in the 2DEG layer stack. Molecules interfere with the upper surface of the 2DEG layer stack, in this case the surface of the AlGaN layer, and have an influence on the 2DEG in the 2DEG layer stack. The sensor also comprises a source and a drain electrode for contacting the 2DEG for measuring an electric characteristic of the 2DEG, more in particular the current between the source and the drain.

However, the gate of the sensor for controlling the electron density of the 2DEG must be kept small in order to provide a sufficiently large surface area between the source and the drain above the 2DEG where the fluidum, in this case gas, molecules can alter an electric characteristic of the 2DEG, such as for example the current between the source and the drain, for example by being adsorbed by the surface area between the source and the drain above the 2DEG. As this limits the dimensions of the gate, which is provided for controlling the electron density of the 2DEG, the control of the electron density in the 2DEG is often insufficient.

Moreover, it has been found that the gate, even with limited dimensions, still reduces the area of the surface where the molecules can influence the 2DEG therefore limiting the sensitivity of the sensor, especially at very low concentrations of the molecules of the fluidum which is desired to be detected.

SUMMARY OF CERTAIN INVENTIVE ASPECTS

In one inventive aspect, there is provided a sensor with which it is possible to improve the control of the electron density of the 2DEG. According to one inventive aspect, the sensitivity of the sensor is improved.

In one inventive aspect, a detection opening is provided between the gate electrode and the 2DEG layer stack and the opening communicates with the space through a detection opening inlet such that fluidum molecules of the fluidum can move from the adjoining space through the detection opening inlet into the detection opening where they can measurably alter a electric characteristic of the 2DEG.

It has been found that with such a configuration, the dimensions of the gate are more independent from the desired sensitivity of the sensor and the gate can overlay, for example, a large part of the 2DEG layer stack and thus of the 2DEG in between the source and the drain, allowing an improved control of the electron density of the 2DEG.

Moreover, such a configuration allows that although the dimensions of the gate overlaying the 2DEG layer can be increased, the sensitivity of the sensor is not affected and is even improved as the 2DEG layer stack underlying the gate but contacting the detection opening can now, for example, be brought into direct contact with molecules of the fluidum which is desired to be detected. The fluidum may be a gas or a fluid.

In one inventive aspect, the 2DEG layer stack comprises a contact surface contacting the detection opening and being provided to contact molecules of the fluidum which is desired to be detected.

In one inventive aspect, the distance between the contact surface and the side of the gate facing the contact surface, i.e. the height of the detection opening, is between about 20 nm and 1500 nm, particularly between about 40 nm and 1000 nm or between about 100 nm and 1000 nm. It has been found that with such height of the detection opening, the electron density can still be sufficiently controlled by the gate voltage while allowing the fluidum molecules to relatively easily move through the detection opening.

In one inventive aspect, the 2DEG layer stack, the source, the drain and the gate form a HEMT (High Electron Mobility Transistor), may be formed, but not limited to, by a heterojunction of III/V materials such as for example III/N materials, such as for example at least one AlGaN layer and a GaN layer on top of each other. As such transistors are reasonably well-understood to the person skilled in the art it has been found that they can be adapted to the fluida which are desired to be detected.

In one inventive aspect, the gate overlays a substantial part of the 2DEG layer stack in between the source and the drain, improving the control of the 2DEG in the 2DEG layer stack.

In one inventive aspect, the 2DEG layer stack comprises a contact surface contacting the detection opening and provided to contact molecules of the fluidum which is desired to be detected and wherein the distance between the 2DEG and the contact surface is about 5 nm to 10 nm, particularly 5.5 nm to 8.5 nm or 6 nm to 7 nm. A 2DEG layer stack having such a reduced thickness in between the 2DEG and the detection opening have been found to be much more sensitive to the presence of molecules of the fluidum. In one inventive aspect, if present, the upper layer of a hetero-junction of the 2DEG layer stack forming the 2DEG, for example a hetero-junction of III/V materials such as for example III/N materials, such as for example at least one AlGaN layer and a GaN layer on top of each other, has a thickness of about 5 nm to 10 nm, particularly 5.5 nm to 8.5 nm or 6 nm to 7 nm.

In one inventive aspect, the detection opening is at least partly filled with a porous material, wherein the pores of the porous material may be adapted to the molecules of the fluidum material which is desired to be detected, for example somewhat bigger than the molecules of the fluidum material which is desired to be detected, and more particularly have a diameter of about 1 nm. Porous material has been found to enhance selectivity with respect to the fluidum material which is desired to be detected by the sensor. In one inventive aspect, the porous material is applied adjoining the 2DEG layer stack, more particularly along the upper layer of the hetero-junction forming the 2DEG. In one inventive aspect, the porous material is provided substantially filling the entire detection opening.

In one inventive aspect, the porous material can for example be porous siliconoxicarbides. However, other porous material such as for example zeolites, polymers and/or solgels are also possible in addition or as a replacement of the porous siliconoxicarbides.

In one inventive aspect, the 2DEG layer stack comprises a contact surface contacting the detection opening and provided to contact molecules of the fluidum which is desired to be detected and wherein the contact surface is provided with a functional layer for binding or adsorbing molecules of the fluidum which is desired to be detected. In one inventive aspect, in addition or alternatively, the gate electrode comprises a contact surface contacting the detection opening and provided to contact molecules of the fluidum which is desired to be detected and wherein the contact surface is provided with a functional layer for binding or adsorbing molecules of the fluidum which is desired to be detected. Such functional layer has been found to further increase the sensitivity of the sensor. Examples of such a functional layer are for example any one of and/or combinations of the following: polymers, redox-active molecules such as phthalocyanines, (metal)porphyrins, biomolecules (DNA, receptors, antibodies, proteins), etc.

In one inventive aspect, the sensor comprises a plurality of respective 2DEG layer stacks, each of the respective 2DEG layer stacks being provided further away from the detection opening inlet. It has been found that such a configuration allows measuring the speed with which the molecules of the fluidum which is desired to be detected diffuse through the detection opening, i.e. the diffusion speed, can be measured. In one inventive aspect, the detection opening is at least partly filled with a porous material, as described above, as it has been found that such a configuration allows measuring the diffusion speed more precisely.

One inventive aspect also relates to the use of the sensor for sensing at least one fluidum, such as a gas or a fluid, in an adjoining space.

In one inventive aspect, a voltage is applied to the gate and the electric characteristic of the 2DEG which is measurably altered by the presence of the fluidum molecules is a current transmitted through the source, the 2DEG and the drain. Such a current has been found easy to measure. Moreover, such a current is also very responsive to any of the fluidum molecules present in the detection opening.

In one inventive aspect, the voltage applied to the gate is such that the 2DEG is present in the 2DEG layer stack without the fluidum molecules present in the detection opening and such that the electron concentration of the 2DEG decreases upon presence of the fluidum molecules. In such configuration, the current measured through the source and drain electrodes will drop significantly upon presence of the fluidum molecules in the detection opening. Such a configuration is also known as a "normally-on configuration".

In one inventive aspect, the voltage applied to the gate is such that the 2DEG is not substantially present in the 2DEG layer stack without the fluidum molecules present in the detection opening and such that the electron concentration of the 2DEG increases upon presence of the fluidum molecules. In such configuration, the current measured through the soured and drain electrodes will increase significantly upon presence of the fluidum molecules in the detection opening. Such a configuration is also known as a "normally-off configuration".

In one inventive aspect, an alternating voltage is applied to the gate. Such an alternating voltage applied to the gate allows to use the electric field in between the gate and the 2DEG and the fluidum in the detection opening as an additional parameter indicating the presence of the fluidum molecules, for example by measuring the current through the source and the drain electrode in function of the alternating voltage. At higher frequencies of the alternating voltage, for example frequencies above 1 kHz, the parameter corresponds to measuring the capacitance between the gate and the 2DEG, wherein the capacitance is influenced by the dielectric properties of the material(s) in the detection opening.

One inventive aspect also relates to a method for making the sensor for sensing at least one fluidum, such as a gas or a fluid, in an adjoining space.

BRIEF DESCRIPTION OF THE DRAWINGS

The disclosure will be further elucidated by means of the following description and the appended figures.

FIG. 1a shows a cross section of an embodiment of the disclosed sensor.

FIG. 1b shows a top view of the embodiment shown in FIG. 1a.

DETAILED DESCRIPTION OF CERTAIN ILLUSTRATIVE EMBODIMENTS

In the following detailed description, numerous specific details are set forth in order to provide a thorough understanding of the disclosure and how it may be practiced in particular embodiments. However, it will be understood that the present disclosure may be practiced without these specific details. In other instances, well-known methods, procedures and techniques have not been described in detail, so as not to obscure the present disclosure. While the present disclosure will be described with respect to particular embodiments and with reference to certain drawings, the disclosure is not limited hereto. The drawings included and described herein are schematic and are not limiting the scope of the disclosure. It is also noted that in the drawings, the size of some elements may be exaggerated and, therefore, not drawn to scale for illustrative purposes.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

1. Sensor
2. 2DEG layer stack
3. Source
4. Drain
5. Gate
6. 2DEG
7. Detection opening
8. Contact surface
9. AlGaN layer
10. GaN layer
11. Porous material
12. Further 2DEG stacks
13. Detection opening inlet FIG. 1a shows a cross section of an embodiment of the disclosed sensor.

The sensor 1 is for sensing the presence of at least one fluidum in a space adjoining the sensor 1. Any type of fluidum, such as for example a gas or a fluid, is possible, for example but not limited to: alcoholic vapors, benzene/tolune/xylene/etc., $CO_2$, CO, $NO_2$, NO, $H_2S$, Formaldehyd, metal ions, etc. The sensor 1 comprises a 2DEG 6 (two-Dimensional Electron Gas) layer stack 2, a gate 5 electrode overlaying at least part of the 2DEG layer stack 2 for electrostatically controlling electron density of a 2DEG in the 2DEG layer stack 2 and a source 3 and a drain 4 electrode contacting the 2DEG layer stack 2 for electrically contacting the 2DEG 6. A detection opening 7 is provided in between the gate 5 electrode and the 2DEG layer stack 2. The detection opening 7 communicates with the space through a detection opening inlet 13 such that molecules of the fluidum can move from the adjoining space through the detection opening inlet 13 into the detection opening 7 where they can measurably alter a electric characteristic of the 2DEG 6. As explained above, the detection opening, more in particular its dimensions, more particularly is adapted to the fluidum which is desired to be detected.

The 2DEG layer stack 2 comprises a contact surface 8 contacting the detection opening 7 and provided to contact molecules of the fluidum which is desired to be detected.

FIG. 1a shows that in one embodiment the 2DEG layer stack 2, the source 3, the drain 4 and the gate 5 form a high electron mobility transistor (HEMT). The HEMT shown is formed by a hetero-junction of III/V materials 9, 10. More in particular, the hetero-junction is formed by III/N materials. Even more in particular, the hetero-junction is formed by at least one AlGaN layer 9 and a GaN layer 10 on top of each other.

In the sensor 1 shown in FIG. 1a the gate 5 overlays a substantial part of the 2DEG layer stack 2 in between the source 3 and the drain 4. This way, as can be seen in FIG. 1a, the gate 5 overlays substantially the entire 2DEG such as to increase the control of the electron density of the 2DEG by the gate 5.

As can be seen in FIG. 1a, the detection opening 7 is at least partly filled with a porous material 11. The porous material may be applied adjoining the 2DEG layer stack, more particularly along the upper layer of the hetero-junction forming the 2DEG, as shown in FIG. 1a. As shown in FIG. 1a, the porous material is provided substantially filling the entire detection opening.

FIG. 1b shows a top view of the sensor of FIG. 1a.

FIG. 1b for example shows the inlet 13 through which molecules of the fluidum can enter the detection opening. The inlet 13 is in the form of the porous material 11, extending out off the detection opening, along which molecules of the fluidum may enter the detection opening.

FIG. 1b further shows that the sensor 1 comprises a plurality of respective 2DEG 6 layer stacks 2, 12, each of the respective 2DEG layer stacks 2 being provided further away from the detection opening 7 inlet 13. Although FIG. 1b shows that the respective source and drain electrodes provided to the further 2DEG layer stacks 12 are different from each other, the respective source and drain electrodes may be interconnected such that the respective sources and the respective drains can be interconnected such as to form a single source and a single drain out off the different respective sources and drains. This is for example illustrated in the gate 5 shown in FIG. 1b which is formed by interconnecting the respective gates of the different 2DEG layer stacks 2, 12. Such a single gate interconnecting the respective gates of the of the respective 2DEG layer stacks 2, 12 is however not critical for the embodiment and the respective gates can also be provided to be individually controlled.

By way of an example, the sensor according to one embodiment can be made by first making the 2DEG layer stack, as is known for the person skilled in the art.

However, for example, before application of the gate material above the 2DEG of the 2DEG layer stack is removed in between the source and the drain, more in particular in between the source and the drain electrodes such as to create the detection opening 7. This can for example be done by etching, after having applied an etch window mask leaving open the area which will be removed by etching and covering the remaining part of the 2DEG layer stack.

Subsequently, porous material is for example deposited where material has been removed from the 2DEG layer stack after which the gate material is applied on top of the porous material. Depending on the application method, part of the porous material and the gate material should be removed, for example from above the source and drain. The partial removal of the gate material and/or the porous material can be done together after application of the gate material or separately, i.e. the part of the porous material to be removed is removed before application of the gate material and the part of the gate material to be removed is removed separately after application of the gate material. Alternatively, the gate can be made independently from the 2DEG layer stack, for example from a different wafer and then placed upside-down on top of the created opening, for example using a spacer. Although the method of placing the prefabricated gate electrode upside-down on the created opening allows to avoid using a porous material or allows to only partially fill the opening with porous material, such an opening can also be created by for example removing, for example fully or partially, the porous material, or any other filling material that was used to temporarily fill the opening, and later removing the filling material, for example by dissolving the material in a fluid. Using this method it becomes possible to functionalize the contact surface of the gate electrode and/or the 2DEG layer stack with a functional layer for binding or adsorbing molecules of the fluidum which is desired to be detected after the at least partial removal of the material below the gate electrode. For example, the functional layer could comprise a molecular layer. For example, this could be a layer of molecules that forms dipoles in the presence of the fluidum, for example gas. In this way the fluidum can for example be detected by a gate voltage shift. Alternatively you can first functionalize a substrate and place this or flip chip bond this on top of the gate area.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A sensor for sensing the presence of at least one fluidum in a space adjoining the sensor, comprising:
    a plurality of laterally arranged two-dimensional electron gas (2DEG) layer stacks;
    a gate electrode overlaying at least part of each of the 2DEG layer stacks and configured to electrostatically control electron densities of a 2DEG in each of the 2DEG layer stacks;
    a plurality of pairs of source and drain electrodes, wherein a source electrode and a drain electrode of each pair contact one of the 2DEG layer stacks and are laterally interposed in a first lateral direction by a contact surface; and
    a detection opening vertically interposed between the gate electrode and the 2DEG layer stacks to form a cavity laterally extending in a second lateral direction crossing the first lateral direction to at least partially overlap the gate electrode,
    wherein the detection opening is at least partly filled with a porous material and configured to communicate with the space through a detection opening inlet by allowing molecules of the fluidum to move from the adjoining space through the detection opening inlet into the detection opening to measurably alter an electric characteristic of the 2DEG in each of the 2DEG layer stacks.

2. The sensor of claim 1, wherein each of the 2DEG layer stacks comprises a contact surface contacting the detection opening and configured to contact molecules of the fluidum to be detected and wherein the distance between the contact surface and the side of the gate electrode facing the contact surface is between about 20 nm and 1500 nm, or between about 40 nm and 1000 nm.

3. The sensor according to claim 1, wherein each of the 2DEG layer stacks, a respective contacting pair of source and drain electrodes and the gate electrode form a high electron mobility transistor (HEMT).

4. The sensor of claim 3, wherein a hetero-junction of HEMT is formed by at least one AlGaN layer and a GaN layer on the at least one AlGaN layer.

5. The sensor of claim 1, wherein the gate electrode overlays a substantial part of each of the 2DEG layer stacks between a respective contacting pair of source and the drain electrodes.

6. The sensor of claim 1, wherein each of the 2DEG layer stacks comprises a contact surface contacting the detection opening and configured to contact molecules of the fluidum to be detected and wherein the distance between the 2DEG and the contact surface is about 5 nm to 10 nm, 5.5 nm to 8.5 nm or 6 nm to 7 nm.

7. The sensor of claim 1, wherein each of the 2DEG layer stacks comprises a contact surface contacting the detection opening and configured to contact molecules of the fluidum to be detected and wherein the contact surface is provided with a functional layer for binding molecules of the fluidum to be detected.

8. The sensor of claim 1, wherein the 2DEG layer stacks are laterally positioned at different distances from the detection opening such that the 2DEG layer stacks are configured to measure a diffusion speed of the molecules of the fluidum based on measurements from a closer one and a farther one of the 2DEG layer stacks.

9. A method of sensing the presence of at least one fluidum, the method comprising using a sensor for sensing the presence of the fluidum in a space adjoining the sensor, the sensor comprising:
    a plurality of laterally arranged two-dimensional electron gas (2DEG) layer stacks;
    a gate electrode overlaying at least part of each of the 2DEG layer stacks and configured to electrostatically control electron densities of a 2DEG in each of the 2DEG layer stacks;
    a plurality of pairs of source and drain electrodes, wherein a source electrode and a drain electrode of each pair contact one of the 2DEG layer stacks and are laterally interposed in a first lateral direction by a contact surface; and
    a detection opening vertically interposed between the gate electrode and the 2DEG layer stacks to form a cavity laterally extending in a second lateral direction crossing the first lateral direction to at least partially overlap the gate electrode,
    wherein the detection opening is at least partly filled with a porous material and configured to communicate with the space through a detection opening inlet by allowing molecules of the fluidum to move from the adjoining space through the detection opening inlet into the detection opening to measurably alter an electric characteristic of the 2DEG in each of the 2DEG layer stacks.

10. The method according to claim 9, the method further comprising applying a voltage to the gate electrode and measuring a current transmitted through the 2DEG and a respective pair of contacted drain and source electrodes that is measurably altered by the presence of the fluidum molecules.

11. The method according to claim 10, wherein the voltage applied to the gate electrode is such that a 2DEG is present in each of the 2DEG layer stacks without the fluidum molecules present in the detection opening and such that the electron concentration of the 2DEG decreases upon presence of the fluidum molecules.

12. The method according to claim 10, wherein the voltage applied to the gate electrode is such that a 2DEG is not substantially present in each of the 2DEG layer stacks without the fluidum molecules present in the detection opening and such that the electron concentration of the 2DEG increases upon presence of the fluidum molecules.

13. The method according to claim 10, wherein an alternating voltage is applied to the gate electrode.

14. A method of making a sensor, the method comprising:
    providing a plurality of laterally arranged two-dimensional electron gas (2DEG) layer stacks,
    providing a gate electrode overlaying at least part of each of the 2DEG layer stacks and configured to electrostatically control electron densities of a 2DEG in each of the 2DEG layer stacks;
    providing a plurality of pairs of source and drain electrodes, wherein a source electrode and a drain electrode of each pair contact one of the 2DEG layer stacks and are laterally interposed in a first lateral direction by a contact surface; and providing a detection opening vertically interposed between the gate electrode and the 2DEG layer stacks to form a cavity laterally extending in a second lateral direction crossing the first lateral direction to at least partially overlap the gate electrode, wherein the detection opening is at least partly filled with a porous material and configured to communicate with the space through a detection opening inlet by allowing molecules of the fluidum to move from the adjoining space through the detection opening inlet into the detection opening to measurably alter an electric characteristic of the 2DEG in each of the 2DEG layer stacks.

15. The sensor of claim 1, wherein the porous material comprises pores having dimensions that are adapted to selectively diffuse molecules of the fluidum through the detection opening.

16. The sensor of claim 15, wherein the pores have a diameter of about 1 nm.

17. The sensor of claim 1, wherein the porous material is selected from the group consisting of porous siliconoxicarbides, zeolites, polymers and solgels.

18. The sensor of claim 1, wherein the porous material substantially fills the entire detection opening.

* * * * *